United States Patent
Ueda

(10) Patent No.: US 9,839,345 B2
(45) Date of Patent: Dec. 12, 2017

(54) ENDOSCOPE HAVING FLEXIBLE TUBE

(71) Applicant: FUJIFILM Corporation, Tokyo (JP)

(72) Inventor: Yoshihiro Ueda, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 539 days.

(21) Appl. No.: 14/496,484

(22) Filed: Sep. 25, 2014

(65) Prior Publication Data

US 2015/0087905 A1    Mar. 26, 2015

(30) Foreign Application Priority Data

Sep. 26, 2013 (JP) .................................. 2013-199845

(51) Int. Cl.
*A61B 1/00* (2006.01)
*A61B 1/005* (2006.01)

(52) U.S. Cl.
CPC ............ *A61B 1/0057* (2013.01); *A61B 1/005* (2013.01); *A61B 1/00078* (2013.01)

(58) Field of Classification Search
CPC .......................... A61B 1/0057; A61B 1/00078
USPC ........................................................ 600/144
See application file for complete search history.

(56) References Cited

U.S. PATENT DOCUMENTS

| | | | | |
|---|---|---|---|---|
| 3,854,473 A | * | 12/1974 | Matsuo | A61B 1/018 128/207.14 |
| 5,179,935 A | * | 1/1993 | Miyagi | A61B 1/0055 600/108 |
| 5,810,715 A | * | 9/1998 | Moriyama | A61B 1/00078 600/139 |
| 5,885,208 A | | 3/1999 | Moriyama | |
| 5,976,074 A | * | 11/1999 | Moriyama | A61B 1/00078 600/139 |
| 6,203,494 B1 | * | 3/2001 | Moriyama | A61B 1/0052 600/144 |
| 8,366,606 B2 | * | 2/2013 | Watanabe | A61B 1/00071 600/104 |
| 8,702,595 B2 | * | 4/2014 | Ueki | A61B 1/0057 600/144 |

(Continued)

FOREIGN PATENT DOCUMENTS

| | | |
|---|---|---|
| JP | 10-305005 A | 11/1998 |
| JP | 2001-258828 A | 9/2001 |
| JP | 2002-360504 A | 12/2002 |

(Continued)

*Primary Examiner* — Matthew J Kasztejna
(74) *Attorney, Agent, or Firm* — Birch, Stewart, Kolasch & Birch, LLP

(57) ABSTRACT

In an endoscope, a flexible device of an elongated tube has a variable stiffness device. The variable stiffness device includes a movable control wire and a coil spring, to which compression force is applied to change stiffness. There occur changes in stiffness of the flexible device in plural radial directions of the coil spring at an equal point in an axial direction. The variable stiffness device is so constructed that a difference between maximum and minimum levels of stiffness of the variable stiffness device is set at most 0.2 time as much as stiffness of the flexible device with internal structures other than the variable stiffness device. Thus, unexpected grip feeling in manipulation of an operator at the time of advance can be removed in relation to undulating motion of the coil spring.

4 Claims, 16 Drawing Sheets

(56) References Cited

U.S. PATENT DOCUMENTS 9,089,259 B2 * 7/2015 Takeuchi ............. A61B 1/0051

FOREIGN PATENT DOCUMENTS

| JP | 2002-360505 A | 12/2002 |
|----|---------------|---------|
| JP | 2003-275167 A | 9/2003 |
| JP | 2012-81011 A | 4/2012 |

* cited by examiner

FIG. 13

| Point in axial direction AD | | Bending stiffness | | | | | |
|---|---|---|---|---|---|---|---|
| | | Initial condition (unadjusted) | | Condition after adjusting bending stiffness before undulating motion | | Condition upon undulating motion after adjusting bending stiffness | |
| | | A | B | A | B | A | B |
| Radial direction | Upward direction U | 1 | 1 | 2 | 2 | 5 | 4 |
| | Left-hand direction L | 1 | 1 | 2 | 2 | 3 | 6 |

ENDOSCOPE HAVING FLEXIBLE TUBE

CROSS-REFERENCE TO RELATED APPLICATION

This application claims priority under 35 USC 119 from Japanese Patent Application No. 2013-199845, filed 26 Sep. 2013, the disclosure of which is incorporated by reference herein.

BACKGROUND OF THE INVENTION

1. Field of the Invention

The present invention relates to an endoscope having a flexible tube. More particularly, the present invention relates to an endoscope having a flexible tube with a coil spring, and in which entry of the flexible tube into a body cavity can be safely performed without influence of undulating motion due to the coil spring.

2. Description Related to the Prior Art

An endoscope includes a grip handle and an elongated tube disposed to extend from the grip handle in a distal direction. The elongated tube is entered in a body cavity of a body, for example, gastrointestinal tract, and includes a rigid tip device, a steering device and a flexible device of a great length. The tip device includes a viewing window and lighting windows disposed at a distal end surface. The steering device is moved by rotation of steering wheels at the grip handle, and bends in upward and downward directions and right hand and left-hand directions. A flexible tube structure is included in the flexible device.

In the flexible device, a direction, orientation and the like of the tip device is difficult to set due to the flexibility. Advance of the tip device to an object of interest in the body cavity is difficult. In view of this, a known type of the endoscope includes a stiffness controller, which is disposed in the flexible tube structure for adjusting flexibility relative to a direction of bending the flexible device. The stiffness controller includes a coil spring and a control wire. The coil spring has a large length and includes coil turns contacting one another. The control wire is disposed through the coil spring. A distal end of the control wire is retained to the coil spring. The control wire retains a proximal end of the coil spring in a condition of allowing pull of the control wire. A rotatable control wheel is disposed on the grip handle, and rotated to pull the control wire, so that stiffness of the flexible device is adjusted by changing a compressed condition of the coil spring.

U.S. Pat. No. 5,885,208 (corresponding to JP-A 10-305005) discloses an example of the stiffness controller for the endoscope. An amount of pull of the control wire is settable for preventing buckling of the coil spring even upon bending the flexible tube structure at 180 degrees with a smallest curvature on a condition of a maximum level of bending stiffness by applying compression force to the coil spring by pulling the control wire. Also, JP-A 2003-275167 discloses another example of the endoscope in which a joint device is disposed between a variable stiffness portion and a portion of a constant stiffness and does not deform plastically even with a smaller bend than the variable stiffness portion and the portion of the constant stiffness. This is for the purpose of raising durability at the time of concentration of bend at the portion with a large difference between the levels of the stiffness.

In the course of entry of the elongated tube into a body cavity, the flexible device of the endoscope having the stiffness controller is set in a somewhat flexible condition in a first portion of a travel path. According to an increase in a length of the entry in the travel path, the stiffness is increased to set the flexible device in a nearly straight form for the purpose of effectively transmitting force of steering, so as to raise the manipulability for entry.

The coil spring for use in the stiffness controller has a sufficiently large length, and includes numerous coil turns of a strand which adjacently contact one another. In case the coil spring is compressed, fine unevenness occurs between the coil turns of the strand even while the flexible device is not flexed. Undulating motion of the coil spring is likely to occur with changes with convexity and concavity in an axial direction.

Upon occurrence of the undulating motion, a convex portion of the coil spring is pushed to the outside more than a concave portion of the coil spring. Reaction force to the compression force is created and results in the bending stiffness of a higher level than the inner side. There occurs variability in the bending stiffness in a circumferential direction, namely variability of the stiffness in radial directions even with an equal point in relation to the axial direction. This variability in the stiffness in the flexible device according to a direction of the bending is likely to give unexpected grip feeling to an operator manipulating the endoscope.

SUMMARY OF THE INVENTION

In view of the foregoing problems, an object of the present invention is to provide an endoscope having a flexible tube with a coil spring, and in which entry of the flexible tube into a body cavity can be safely performed without influence of undulating motion due to the coil spring.

In order to achieve the above and other objects and advantages of this invention, an endoscope having an elongated tube for entry in a body cavity and imaging of an object is provided, and includes a flexible tube structure for constituting the elongated tube. A coil spring is contained in the flexible tube structure to extend in an axial direction, for constituting a variable stiffness device. A wire is disposed to extend in the axial direction, received through the coil spring, a distal end of the coil spring being retained on the wire, for constituting the variable stiffness device. An internal structure is contained in the flexible tube structure. An externally operable stiffness controller changes coil tightness of the coil spring by use of the wire, to adjust bending stiffness of the elongated tube. In case the bending stiffness is changed in one radial direction at an equal point with reference to the axial direction, a difference between maximum and minimum levels of bending stiffness of the variable stiffness device is at most 0.2 time as much as bending stiffness of the flexible tube structure inclusive of the internal structure other than the variable stiffness device upon occurrence of undulating motion of the coil spring in response to compression force of the stiffness controller to the coil spring.

Preferably, furthermore, an easily bendable portion is formed with at least one of the coil spring and the wire.

Preferably, the stiffness controller includes a take-up pulley on which a proximal end of the wire is retained, the take-up pulley winding the wire in the axial direction. There is a control wheel rotatable around the axial direction. A first bevel gear is caused to rotate by the control wheel. A second bevel gear is meshed with the first bevel gear, for transmitting rotation to the take-up pulley.

In another preferred embodiment, the stiffness controller includes a slider, movable in the axial direction, for sliding a proximal end of the coil spring relative to a proximal end of the wire. There is a control wheel rotatable around the axial direction. An intermediate gear is caused to rotate by the control wheel. A rack gear is meshed with the intermediate gear, for moving in the axial direction, to transmit movement to the slider.

Preferably, the elongated tube includes a steering device disposed at a distal end of the flexible tube structure in a bendable manner. The wire is disposed to extend to the distal end of the flexible tube structure in the axial direction.

Preferably, the internal structure is constituted by at least a light guide device and a signal cable.

Also, an endoscope having an elongated tube for entry in a body cavity and imaging of an object is provided, and includes a flexible tube structure for constituting the elongated tube, wherein bending stiffness of the flexible tube structure is different in an axial direction. A coil spring is contained in the flexible tube structure to extend in the axial direction, for constituting a variable stiffness device. A wire is disposed to extend in the axial direction, received through the coil spring, a distal end of the coil spring being retained on the wire, for constituting the variable stiffness device. An internal structure is contained in the flexible tube structure. An externally operable stiffness controller changes coil tightness of the coil spring by use of the wire, to adjust the bending stiffness of the elongated tube. In case the bending stiffness is changed in one radial direction at an equal point with reference to the axial direction, a difference between maximum and minimum levels of bending stiffness of the variable stiffness device is at most 0.2 time as much as minimum bending stiffness of the flexible tube structure inclusive of the internal structure other than the variable stiffness device in the axial direction upon occurrence of undulating motion of the coil spring in response to compression force of the stiffness controller to the coil spring.

Preferably, furthermore, an easily bendable portion is formed with at least one of the coil spring and the wire.

Also, an endoscope having an elongated tube for entry in a body cavity and imaging of an object, is provided, and includes a flexible tube structure for constituting the elongated tube. A coil spring is contained in the flexible tube structure to extend in an axial direction, for constituting a variable stiffness device. A wire is disposed to extend in the axial direction, received through the coil spring, a distal end of the coil spring being retained on the wire, for constituting the variable stiffness device. An easily bendable portion is formed with at least one of the coil spring and the wire. An externally operable stiffness controller changes coil tightness of the coil spring by use of the wire, to adjust bending stiffness of the elongated tube.

Preferably, furthermore, an image sensor forms an image of the object through a tip of the elongated tube. The easily bendable portion is disposed on upper or lower side with reference to the image in the coil spring or the wire.

Preferably, furthermore, an indicia is disposed on the variable stiffness device, for indicating a bending direction of the easily bendable portion.

Preferably, the coil spring includes a strand wound in plural coil turns around the axial direction. The easily bendable portion is defined by partially decreasing a thickness of the strand.

Preferably, the easily bendable portion is disposed on the coil turns and in a particular radial direction from the axial direction, and has a strand cross section of a locally long shape in the radial direction.

In another preferred embodiment, the easily bendable portion includes a chamfered surface, formed on one side or two sides of the plural coil turns in the axial direction and in a particular radial direction from the axial direction, for partially decreasing the thickness of the strand.

In still another preferred embodiment, the easily bendable portion is disposed on the coil turns and in a particular radial direction from the axial direction, and has a strand cross section in a rectangular quadrilateral shape.

Preferably, a strand cross section of the strand is in a rectangular quadrilateral shape.

Preferably, an angular range of the easily bendable portion in the coil spring is equal to or less than 180 degrees in a circumferential direction defined around the axial direction.

Preferably, the elongated tube includes a steering device disposed at a distal end of the flexible tube structure in a bendable manner. The wire is disposed to extend to the distal end of the flexible tube structure in the axial direction.

Preferably, the elongated tube includes a steering device disposed at a distal end of the flexible tube structure in a bendable manner. The easily bendable portion is disposed to extend from the distal end of the flexible tube structure toward a proximal end side of the flexible tube structure in the axial direction.

Consequently, entry of the flexible tube into a body cavity can be safely performed without influence of undulating motion due to the coil spring, because stiffness of the coil spring can be controlled suitably in view of suppressing influence of undulating motion.

BRIEF DESCRIPTION OF THE DRAWINGS

The above objects and advantages of the present invention will become more apparent from the following detailed description when read in connection with the accompanying drawings, in which:

FIG. 13 is a table illustrating levels of the stiffness in the conditions of FIGS. 10-12;

DETAILED DESCRIPTION OF THE PREFERRED EMBODIMENT(S) OF THE PRESENT INVENTION

Figure 1:
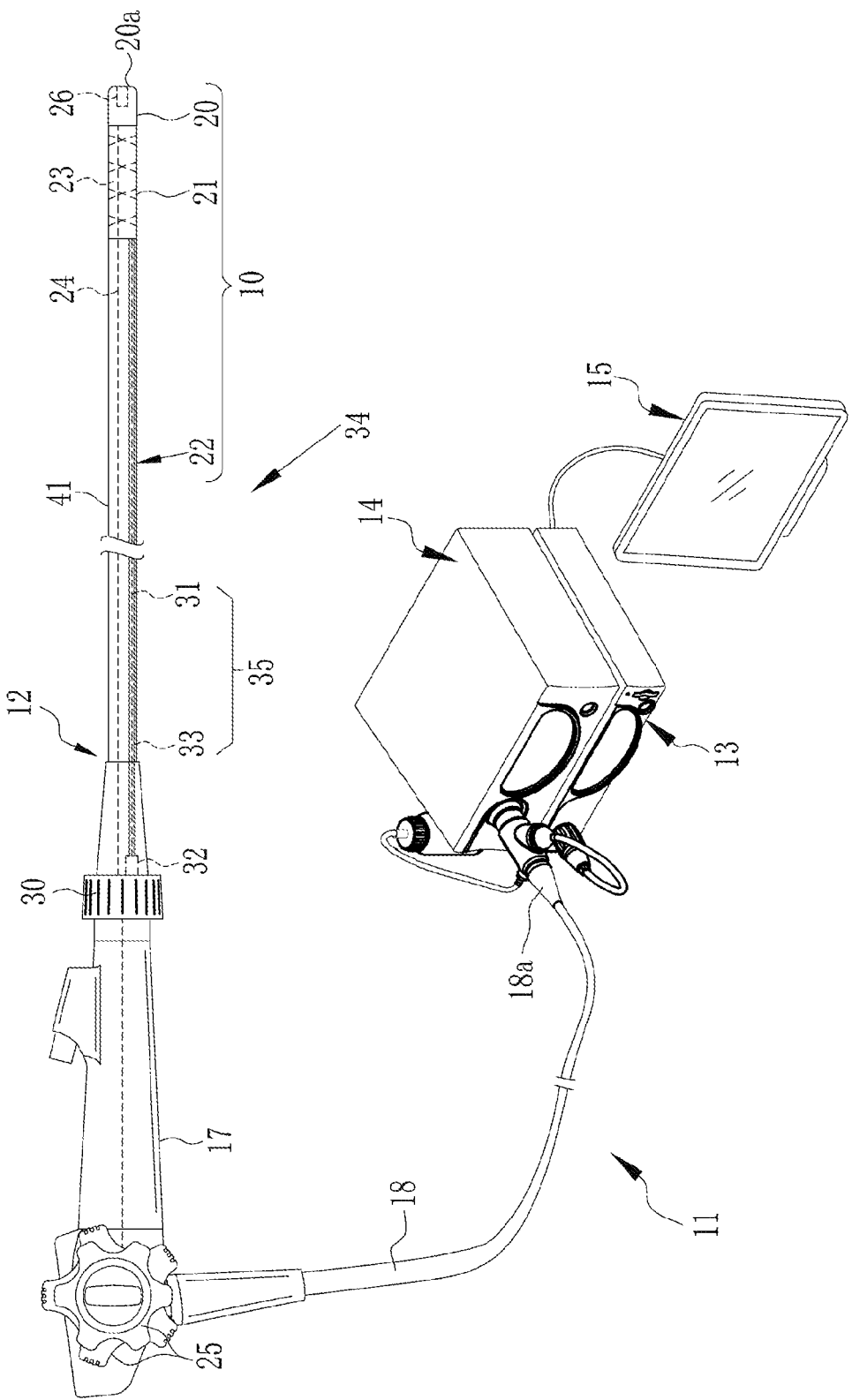
FIG. 1 is an explanatory view illustrating an endoscope system.

In FIG. 1, an endoscope system 11 is illustrated. The endoscope system 11 includes an endoscope 12, a processing apparatus 13, a light source apparatus 14 and a monitor display panel 15. The processing apparatus 13 processes an image signal from the endoscope 12. The light source apparatus 14 supplies the endoscope 12 with light for illumination. The endoscope 12 includes an elongated tube 10 (elongated tube assembly), a grip handle 17 and a universal cable 18. The elongated tube 10 is entered in a body cavity. The grip handle 17 is disposed at a proximal end of the elongated tube 10. The universal cable 18 has a connector 18a for connection with the processing apparatus 13 and the light source apparatus 14.

The elongated tube 10 includes a rigid tip device 20, a steering device 21 and a flexible device 22 arranged in a proximal direction. An image sensor 26 is incorporated in the tip device 20. The steering device 21 is bendable up and down and to the right and left. The flexible device 22 extends from the steering device 21 to the grip handle 17 with a great length.

Plural link elements 23 are connected with one another in a rotatable manner with axial pins, and arranged in an axial direction (AD) to constitute the steering device 21. Steering wires 24 are extended through the link elements 23 and positioned in respectively four positions on an inner surface of the steering device 21. Two steering wheels 25 are disposed on the grip handle 17, and rotated to move the steering wires 24 distally or proximally, to bend the steering device 21 in a desired one of the four directions at a suitable angle. A distal end surface 20a of the tip device 20 is directed by steering of the steering device 21, so that the image sensor 26 can image an object of interest for diagnosis.

The endoscope 12 has a stiffness controller 34 for changing stiffness of the flexible device 22. The stiffness controller 34 includes a variable stiffness device 35 or variable stiffness support, a transmission mechanism 32 and a rotatable control wheel 30 for stiffness adjustment. The variable stiffness device 35 includes a coil spring 33 (helical coil) and a control wire 31 disposed to extend through the coil spring 33. The transmission mechanism 32 responds to rotation of the control wheel 30 and pulls the control wire 31 to apply compression force to the coil spring 33. The transmission mechanism 32 converts rotational movement of the control wheel 30 to linear movement for moving the control wire 31. The control wheel 30 is disposed on the grip handle 17 in a rotatable manner. Note that various types of mechanisms for the stiffness controller 34 other than the control wheel 30 can be used, for example, a lever mechanism, dial mechanism and the like.

Figure 2:
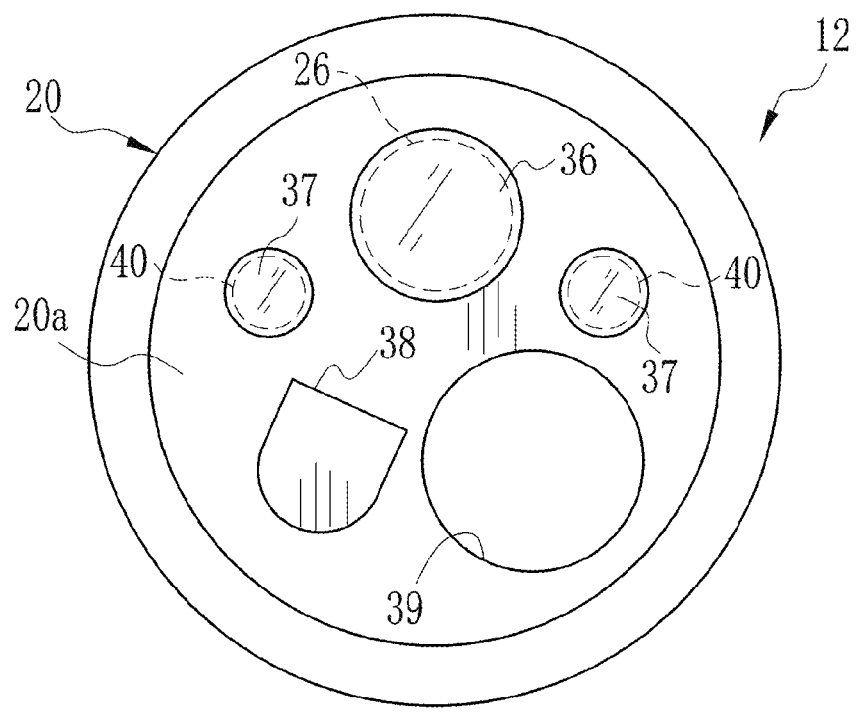
FIG. 2 is a front elevation illustrating a distal end surface of an endoscope.

In FIG. 2, the distal end surface 20a of the endoscope 12 is illustrated in a front elevation. The distal end surface 20a has a viewing window 36, lighting windows 37, a nozzle spout 38 and a distal instrument opening 39. The viewing window 36 passes image light to the image sensor 26. The lighting windows 37 emit light for illumination. The nozzle spout 38 ejects fluid toward the viewing window 36. The distal instrument opening 39 is used for extending a medical instrument, for example, forceps. A lighting head 40 or lighting lens system is disposed behind the lighting windows 37.

Figure 3:
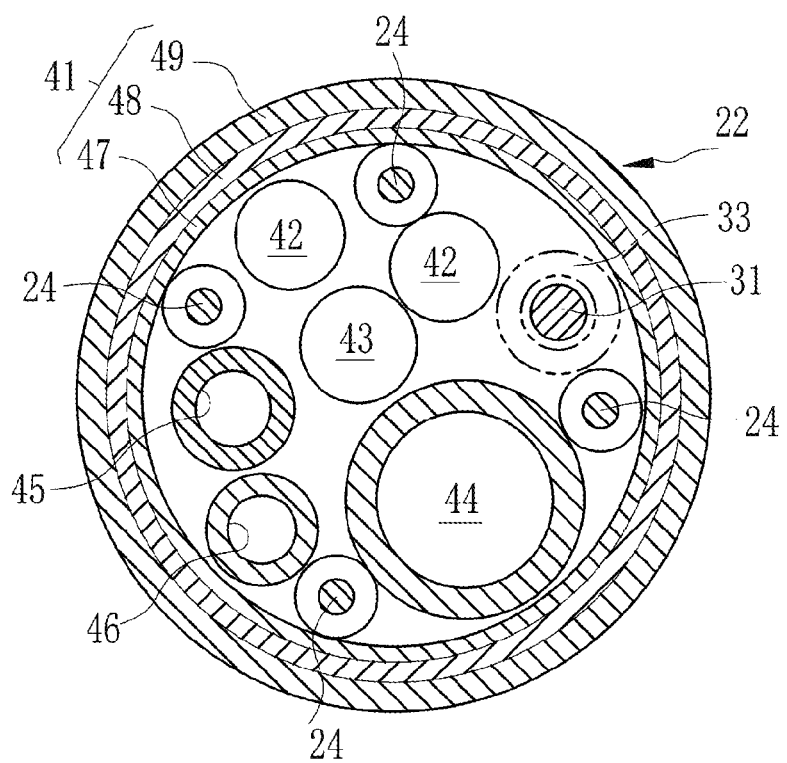
FIG. 3 is a cross section illustrating a flexible device in an elongated tube.

In FIG. 3, the flexible device 22 is illustrated in a section. The flexible device 22 includes a flexible tube structure 41 and plural internal structures in the flexible tube structure 41. The internal structures include a light guide device 42, a signal cable 43, the steering wires 24, an instrument channel 44, an air flow channel 45, a water flow channel 46, the control wire 31 and the coil spring 33. The light guide device 42 guides light to the lighting head 40. The signal cable 43 sends a signal to and receives a signal from the image sensor 26. The flexible tube structure 41 includes a coil winding 47 or helical tubing, a tubular mesh material 48 or mesh tubing, and jacket material 49. The tubular mesh material 48 is disposed around the coil winding 47. The jacket material 49 is around the tubular mesh material 48, and encapsulates the tubular mesh material 48 with the coil winding 47. An example of the jacket material 49 is rubber or resin with elasticity and flexibility.

Figure 4:
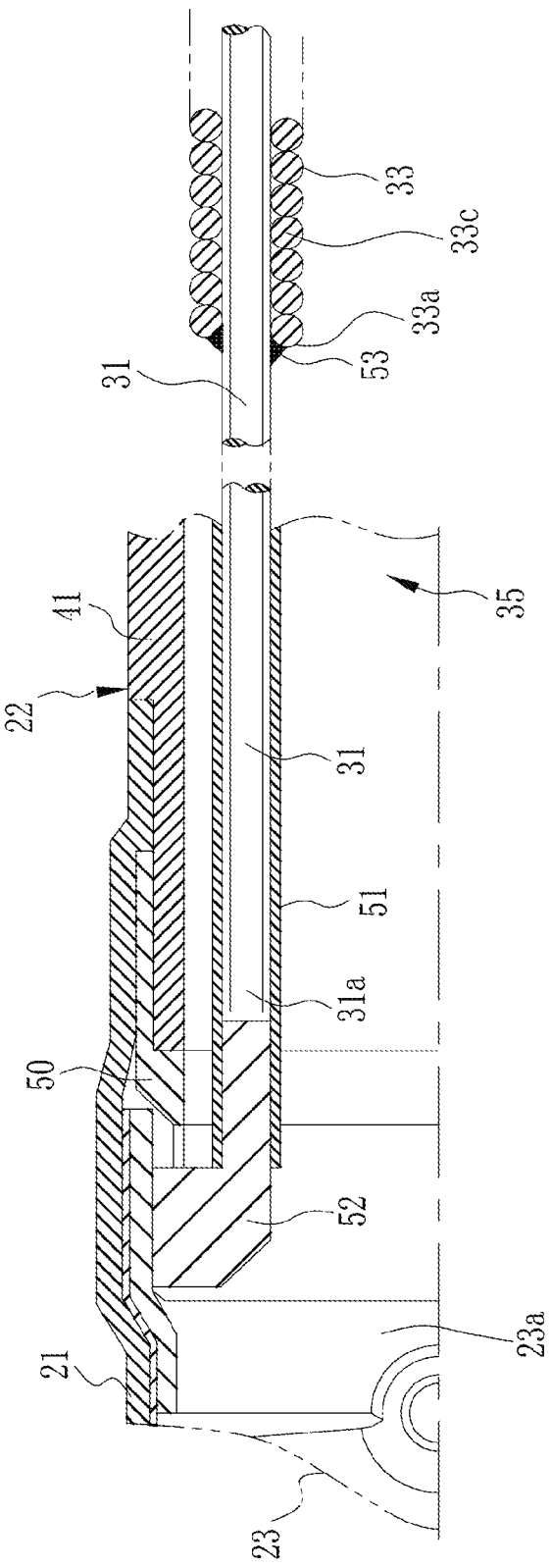
FIG. 4 is a vertical section illustrating a variable stiffness device contained in the endoscope and having a wire and a coil spring

In FIG. 4, arrangement of the control wire 31 and the coil spring 33 of the stiffness controller 34 is illustrated on a distal side for containment in the endoscope 12. A coupling ring 50 is disposed internally between the steering device 21 and the flexible device 22. A proximal link element 23a among the link elements 23 at its proximal end is coupled to the flexible tube structure 41 by the coupling ring 50. The coupling ring 50 has a plug-in coupling 52. An end of a coupling sleeve 51 is fitted on the plug-in coupling 52. The control wire 31 has a distal wire end 31a. The control wire 31 is entered in the coupling sleeve 51 by advancing the distal wire end 31a, to retain the distal wire end 31a on the coupling sleeve 51 fixedly. The coil spring 33 has a distal coil end 33a. Wax binder 53 is applied to the distal coil end 33a for attachment to the control wire 31 in a range extended proximally from the coupling sleeve 51. In the coil spring 33, a strand 33c or filament of a circular shape in a strand cross section is wound in a coil form in a condition of tight contact between its coil turns. Note that it is possible to couple the flexible tube structure 41 directly to the proximal link element 23a of the steering device 21 without using the coupling ring 50. Also, various methods can be used to attach the distal coil end 33a to the control wire 31, without using the coupling sleeve 51.

Figure 5:
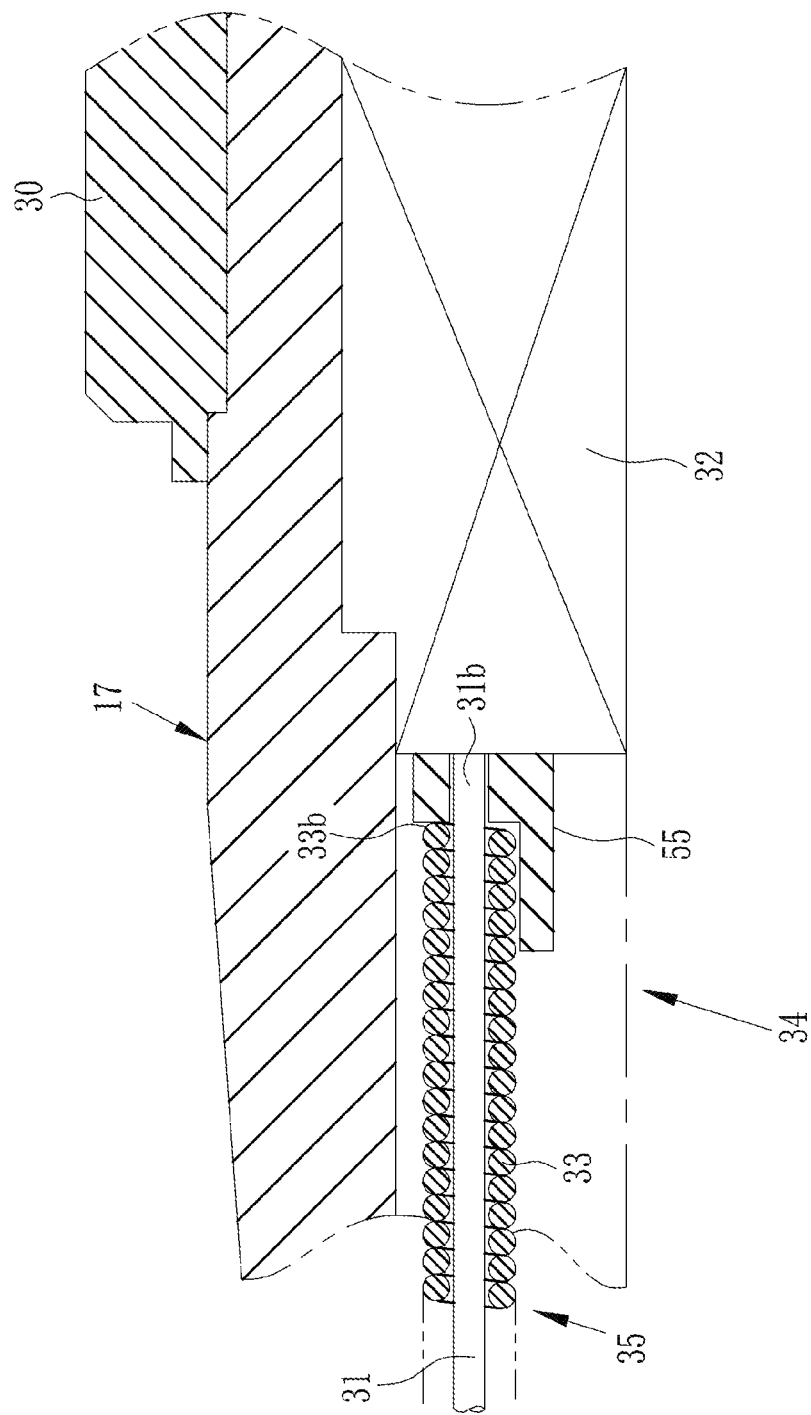
FIG. 5 is a vertical section illustrating arrangement of the wire and the coil spring.

In FIG. 5, arrangement of a proximal wire end 31b of the control wire 31 and a proximal coil end 33b of the coil spring 33 is illustrated. The proximal wire end 31b of the control wire 31 is coupled with the transmission mechanism 32 disposed inside the control wheel 30. An end stopper 55 is disposed in the transmission mechanism 32 and retains the proximal coil end 33b of the coil spring 33. The end stopper 55 presses the proximal coil end 33b while pull of the control wire 31 is allowed. The control wire 31 is moved relative to the coil spring 33 in response to rotation of the control wheel 30, so that the control wire 31 applies compression force to the coil spring 33 to vary the stiffness of the variable stiffness device 35.

Figure 6:
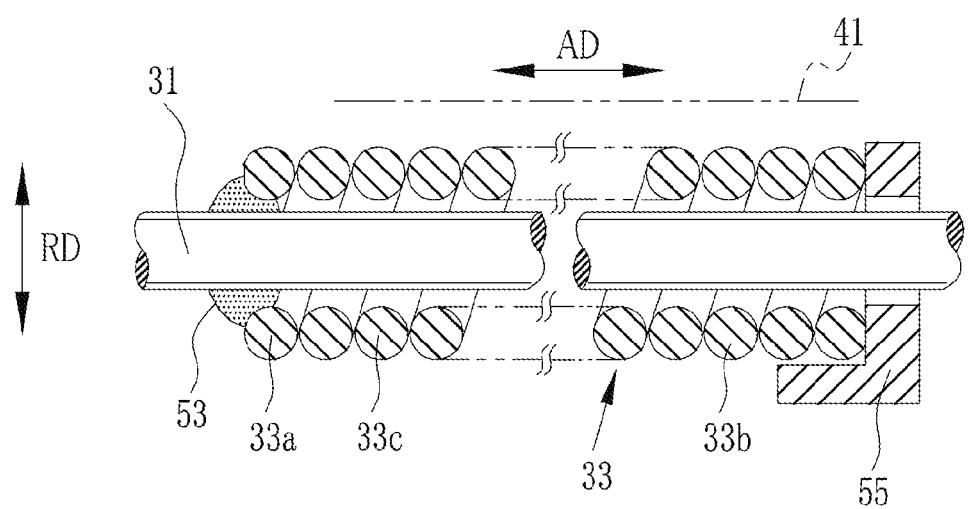
FIG. 6 is a cross section illustrating coil spring.

In FIG. 6, the entirety of the coil spring 33 is illustrated. The wax binder 53 on the control wire 31 attaches the distal coil end 33a of the coil spring 33. The proximal coil end 33b is kept from dropping on the end stopper 55 while the coil spring 33 is contained in the flexible tube structure 41.

Figure 7:
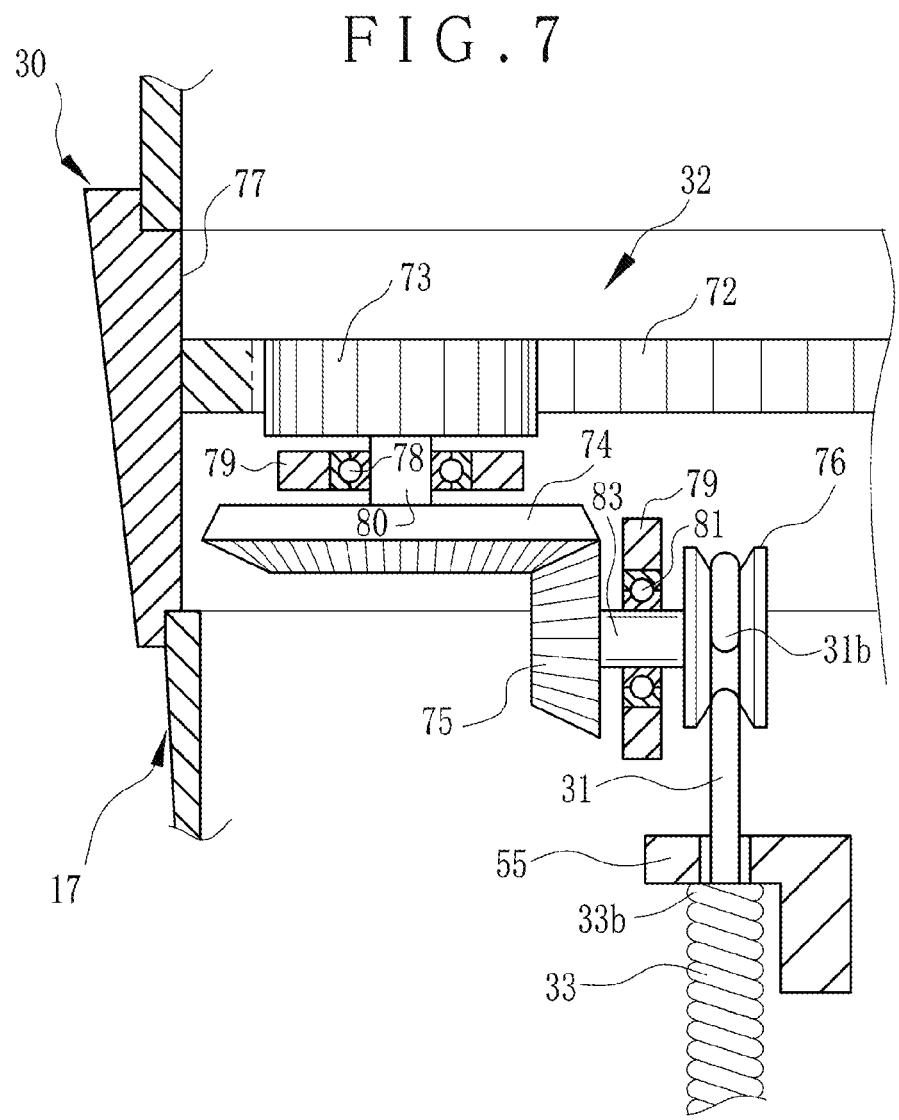
FIG. 7 is a vertical section illustrating a grip handle with a transmission mechanism for driving the wire.

In FIG. 7, the grip handle 17 is illustrated in a section, with a preferred example of the transmission mechanism 32 for transmitting movement of the control wheel 30 to the control wire 31. The transmission mechanism 32 includes an inner gear 72, a spur gear 73, a first bevel gear 74, a second bevel gear 75 and a take-up pulley 76. The control wheel 30 has an inner wall 77, on which the inner gear 72 is formed, and meshed with the spur gear 73. A gear shaft 80 is supported on a handle housing 79 of the grip handle 17. A shaft bearing 78 keeps the spur gear 73 rotatable on one end of the gear shaft 80. The first bevel gear 74 is retained on a second end of the gear shaft 80. The second bevel gear 75 is meshed with the first bevel gear 74. A gear shaft 83 is supported by the handle housing 79. A shaft bearing 81 keeps the second bevel gear 75 rotatable with one end of the gear shaft 83. The take-up pulley 76 is retained on a second end of the gear shaft 83. The control wire 31 is engaged with the take-up pulley 76, and has the proximal wire end 31b attached fixedly to the take-up pulley 76. The end stopper 55 is disposed near to the take-up pulley 76 for positioning the proximal coil end 33b of the coil spring 33.

In case the control wheel 30 is rotated, the spur gear 73 meshed with the inner gear 72 is rotated. The first bevel gear 74 is rotated by the gear shaft 80 and the spur gear 73. The second bevel gear 75 meshed with the first bevel gear 74 is rotated. The take-up pulley 76 is rotated by the second bevel gear 75 and the gear shaft 83, to pull the control wire 31. Note that a worm gear and a worm wheel can be used in place of the first and second bevel gears 74 and 75.

Figure 8:
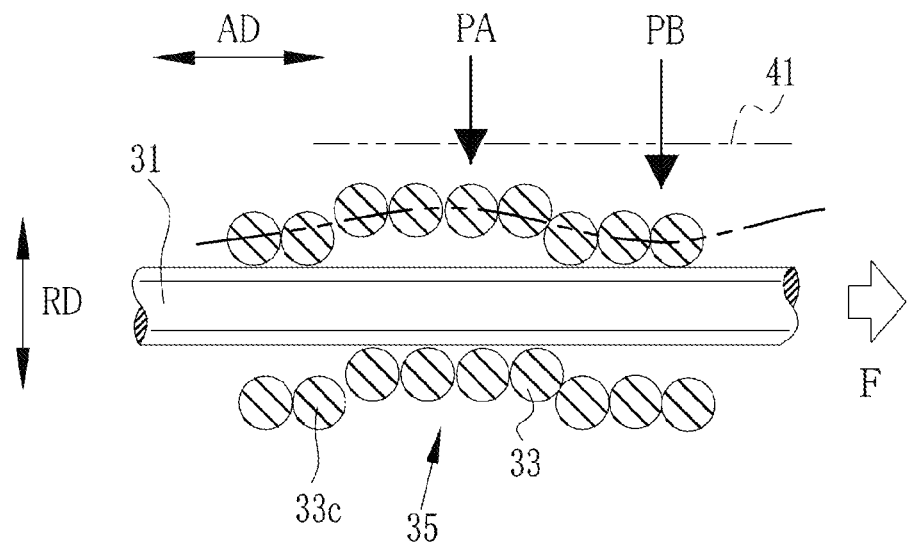
FIG. 8 is a vertical section illustrating occurrence of undulating motion in the coil spring.

In FIG. 8, a condition of the coil spring 33 with undulating motion is illustrated in a section. Even while the flexible tube is not flexed, fine shift between coil turns of the strand 33c occurs continuously in response to compression force of a high level, to create undulating motion.

In view of preventing undulating motion, it is desired to set an inner diameter of the coil spring 33 nearly equal to an outer diameter of the control wire 31 to minimize a clearance space between those. However, a clearance space of a small sufficient size must be kept between the control wire 31 and the coil spring 33 with a small diameter before the control wire 31 can be entered in the coil spring 33. Should friction occur between those, relative movement of the control wire 31 to the coil spring 33 may be impossible. It follows that a suitable clearance space is required between the coil spring 33 and the control wire 31. A small undulating motion is created with the coil spring 33 by the form of the clearance space. In response to the undulating motion of the coil spring 33, a portion (pull side) of the point PA of the flexible device 22 in a convex shape toward the flexible tube structure 41 in an axial direction AD comes to have a higher stiffness. A portion (compression side) of a point PB of the flexible device 22 in a concave shape in the axial direction comes to have a lower stiffness.

Figure 9:
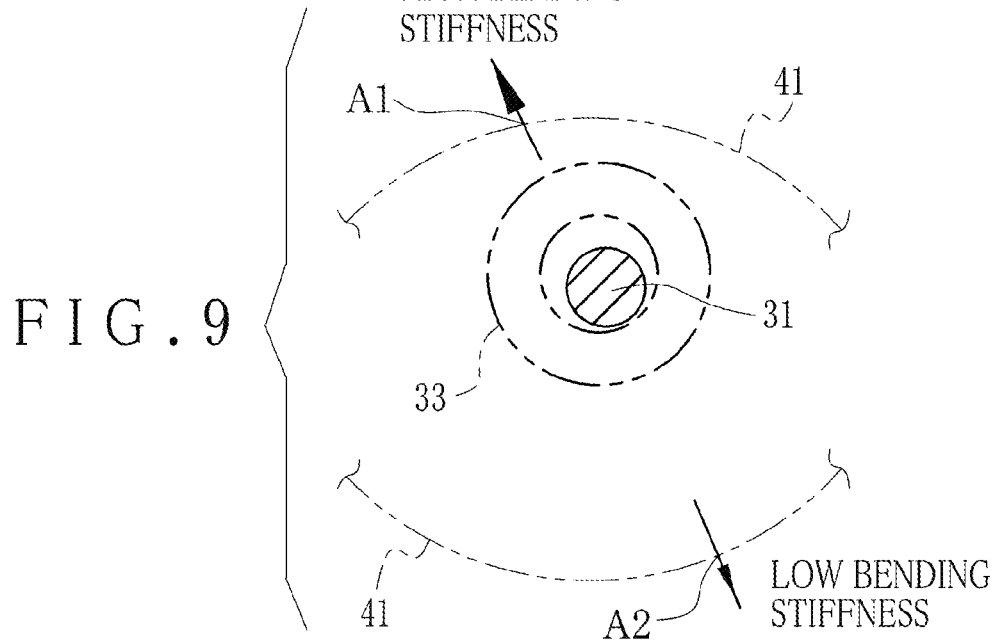
FIG. 9 is an explanatory view in a section illustrating differences in the stiffness between plural radial directions.

FIG. 9 illustrates variations in the stiffness in plural radial directions RD defined around the axial direction AD at the point PA in FIG. 8. Upon occurrence of undulating motion in the coil spring 33, variability in the stiffness in the circumferential direction occurs, as property of a difference in the stiffness between the plural radial directions A1 and A2 in the circumferential direction at the point PA. In FIG. 9, the stiffness increases in the radial direction A1 as an outer position of the convexly curved shape toward the flexible tube structure 41, and decreases in the radial direction A2 as an inner position of the curved shape.

Figure 10:
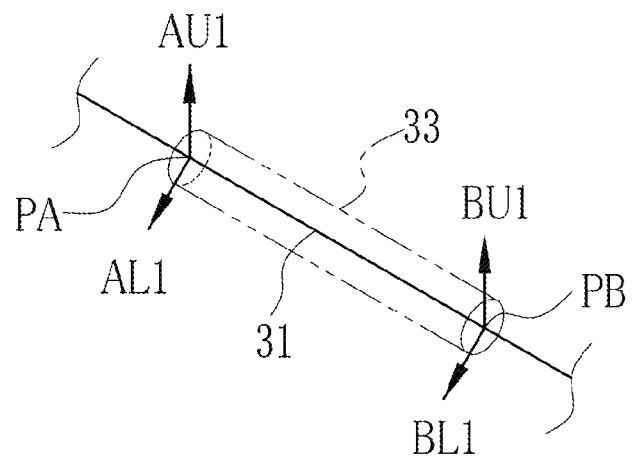
FIG. 10 is an explanatory view in a perspective illustrating distribution of the stiffness in an initial condition without adjustment.
Figure 11:
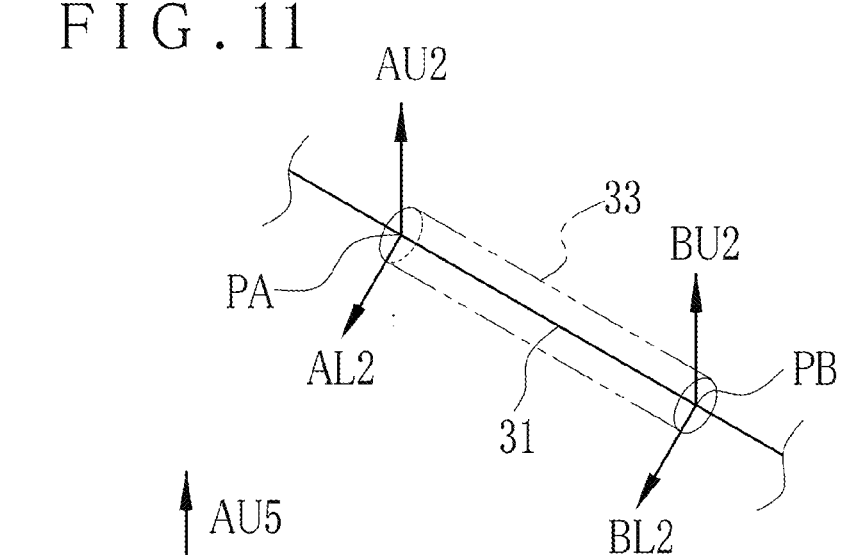
FIG. 11 is an explanatory view in a perspective illustrating distribution of the stiffness in a condition short of occurrence of undulating motion.
Figure 12:
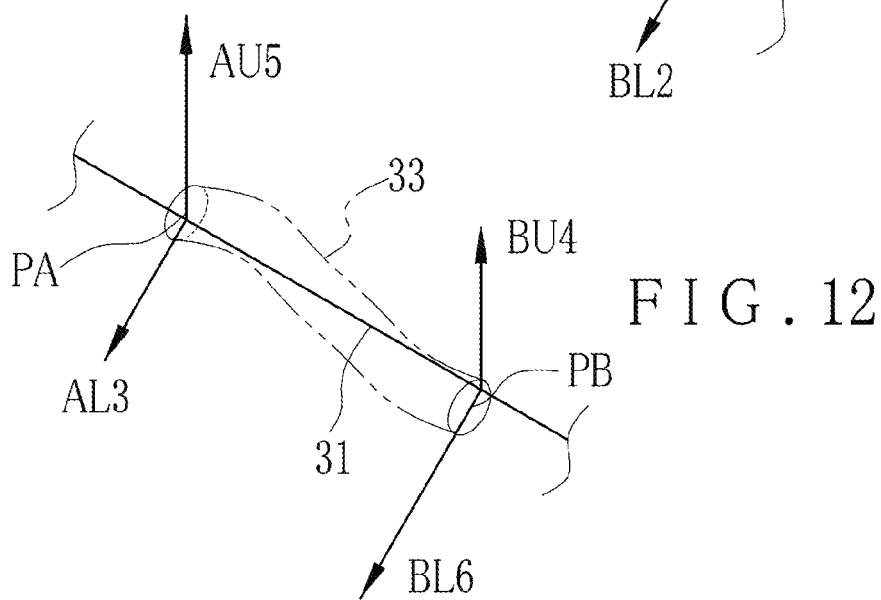
FIG. 12 is an explanatory view in a perspective illustrating distribution of the stiffness in a condition upon the occurrence of undulating motion.

In FIGS. 10-12, examples of stiffness of the coil spring 33 are indicated by vectors, in plural radial directions arranged about the axis at the points PA and PB upon bending the steering device 21 in one direction. In FIG. 10, an initial condition without adjusting the stiffness is illustrated. In FIG. 11, a condition of the coil spring 33 shortly before undulating motion during the stiffness adjustment is illustrated. In FIG. 12, a condition of the coil spring 33 in the undulating motion is illustrated while compression force is applied to the coil spring 33, for increasing the stiffness. In FIG. 13, examples of the stiffness in the conditions of FIGS. 10-12 are illustrated.

In FIGS. 10 and 13, the coil spring 33 is in the initial condition without undulating motion. Signs AU1, AL1, BU1 and BL1 denote levels of stiffness at the point PA in the upward direction, at the point PA in the left-hand direction, at the point PB in the upward direction, and at the point PB in the left-hand direction. The left-hand and upward directions are examples of radial directions RD. In FIGS. 11 and 13, the coil spring 33 is in a condition receiving compression force and immediately before occurrence of undulating motion. Signs AU2, AL2, BU2 and BL2 denote levels of stiffness at the point PA in the upward direction, at the point PA in the left-hand direction, at the point PB in the upward direction, and at the point PB in the left-hand direction. In FIG. 11, a length of the vectors is larger than that in FIG. 10, as the levels of the stiffness are higher than those of FIG. 10.

In FIGS. 12 and 13, a condition with the undulating motion of the coil spring 33 is illustrated. The stiffness in the upward direction and the left-hand direction is denoted by AU5, AL3, BU4 and BL6, as examples of radial directions RD in the point PA and the point PB with a small distance from the point PA. In response to the undulating motion of the coil spring 33, variability in the stiffness in the circumferential direction occurs. The stiffness in the upward and left-hand directions in each of the positions is changed in a sequence of the levels 5, 3, 4 and 6. A length of the vectors changes to create the variability in the stiffness in the circumferential direction. It is likely that the condition makes an operator to have unexpected grip feeling in the course of the steering for the advancement.

Figure 14:
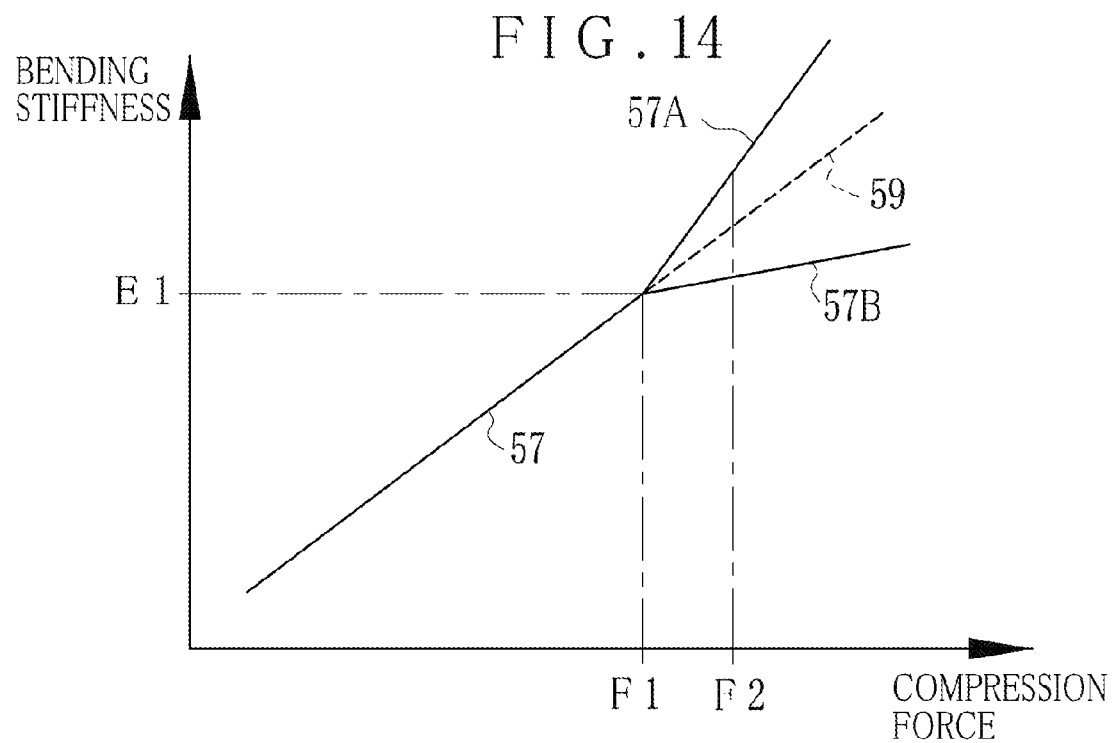
FIG. 14 is a graph illustrating a relationship between the stiffness and compression force.

In FIG. 14, a relationship between compression force of the coil spring 33 and stiffness of the flexible device 22 is illustrated in a graph. In an ideal condition, the relationship is a proportional relation as indicated by a straight solid line 57 and a broken line 59 even upon an increase of the compression force. However, should the compression force be higher than F1, the stiffness in the circumferential direction may increase as indicated by a straight solid line 57A, or may decrease as indicated by a straight solid line 57B. At the points PA and PB with a variation in the curved form of the undulating motion in FIG. 8, occurrence of undulating motion of the coil spring 33 changes the stiffness as indicated by the straight solid lines 57A and 57B in the circumferential direction with reference to the compression force F1.

To prevent the undulating motion of the coil spring 33, it is preferable to set the compression force of the coil spring 33 in a range free from occurrence of variability in the stiffness of the flexible device 22 in the circumferential direction. For example, the compression force of the coil spring 33 is set smaller than the compression force F1. Thus, no variability occurs in the stiffness of the flexible device 22 in the circumferential direction. To be precise, a stiffness range in which the stiffness of the flexible device 22 can be changed by the stiffness controller 34 is determined slightly smaller than the bending stiffness E1 of the flexible device 22 at a level of starting the undulating motion of the coil spring 33. It is preferable previously to obtain the bending stiffness E1 by experiments or the like, because of its differences due to a diameter, material and the like of the strand.

Figure 15:
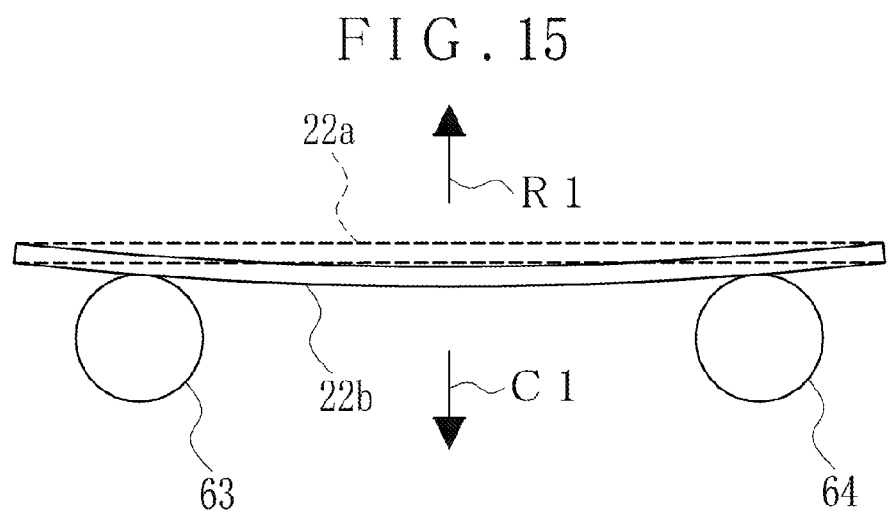
FIG. 15 is a side elevation illustrating a structure for an experiment for acquiring a threshold of the stiffness.

In FIG. 15, an experiment for determining stiffness slightly short of the bending stiffness E1 of the flexible device 22 of a start of undulating motion of the coil spring 33. A broken line for a flexible device 22a denotes a condition of the coil spring 33 without undulating motion. A solid line for a flexible device 22b denotes a condition of the coil spring 33 with undulating motion. A pair of test support devices 63 and 64 arranged at a predetermined interval support the flexible devices 22a and 22b. A predetermined force is applied in a radial direction C1 to the flexible devices 22a and 22b between the test support devices 63 and 64, to measure reaction force R1 (counter force) against the application of the force in the radial direction C1. The measurement of the reaction force R1 is conducted by changing compression force, namely changing stiffness of the flexible device 22. Undulating motion is created upon increasing the compression force.

Figure 16:
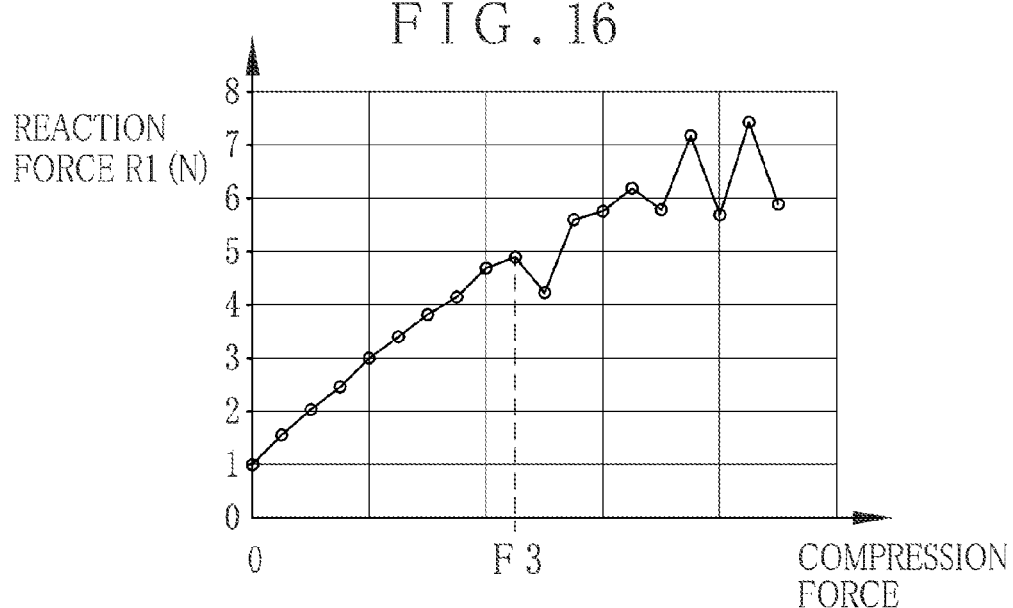
FIG. 16 is a graph illustrating a relationship between reaction force and the compression force.

In FIG. 16, results of the experiments are illustrated in a graph. In the graph, correlation between stiffness or reaction force R1 (N) against compression and a compression force is indicated. The reaction force R1 against the compression increases linearly in a range from 0 to F3 of the compression force, but comes to fluctuate up and down without a constant increase over the compression force F3. A reason for the fluctuation of the reaction force R1 is that the stiffness changes according to a direction of the compression upon occurrence of variability in the stiffness in the circumferential direction with the flexible device 22 by the undulating motion of the coil spring 33. For example, the reaction force R1 of the flexible device 22 shortly before the start of the undulating motion of the coil spring 33 is 5 N. Should a tolerable level of the reaction force R1 shortly before the undulating motion in the embodiment be set equal to a threshold level of the reaction force R1 shortly before the fluctuation, then it is likely that influence of unwanted factors is received, for example, errors in the measurement, unevenness in the stiffness in the material, and the like. Consequently, it is preferable to determine a safety ratio of force in consideration of the unwanted factors. A preferred example of the safety ratio in the embodiment is 0.8. A preferable tolerable level of the reaction force R1 in consideration of the safety ratio is 0.8 time as high as the threshold level of the reaction force R1 for the stiffness of the flexible device 22 shortly before the undulating motion according to results of the experiment, namely, $R1=5N\times 0.8=4N$.

It is preferable that the maximum stiffness of the flexible device 22 is included in a stiffness range of stiffness of the stiffness controller 34. However, should the stiffness range of the stiffness controller 34 be set 0.8 time as high as the stiffness of the flexible device 22 slightly short of occurrence of undulating motion, it is likely that the compression force to the coil spring 33 is discontinued before obtaining the maximum stiffness of the flexible device 22 in the circumferential direction. A width of changes of the stiffness range depends upon a radius of the coil spring 33. Should the stiffness range of the stiffness controller 34 be set equal to stiffness of the flexible device 22 slightly short of the stiffness E1 of the flexible device 22 in occurrence of undulating motion, a problem is likely to arise in that one portion of the stiffness range according to the radius of the coil spring 33 cannot be utilized. In view of this, manipulation with the control wheel 30 is disabled by the control before reach to the compression force F2 with which an operator recognizes variability of the stiffness in the circumferential direction of the flexible device 22 even upon occurrence of a small undulating motion. To this end, there is provided a device for increasing the compression force of the coil spring 33 until the reach to the compression force F2.

The compression force F2 is set according to a sum of first bending stiffness of the internal structures other than the variable stiffness device 35 in the flexible tube structure 41 and second bending stiffness of the flexible tube structure 41 in the circumferential direction. Assuming that the first and second bending stiffness is relatively larger than that of the variable stiffness device 35, no problem occurs with variability in the bending stiffness of the flexible device 22 in the circumferential direction. In case undulating motion occurs in the coil spring 33 due to compression of the coil spring 33 with the stiffness controller 34, the bending stiffness of the flexible device 22 in a given radial direction RD around the axial direction AD and in relation to an equal point in the axial direction AD of the flexible device 22. Thus, a difference between maximum and minimum levels of the bending stiffness of the variable stiffness device 35 is set equal to or less than 0.2 time of the bending stiffness of the flexible device 22 including internal structures other than the variable stiffness device 35. Therefore, the operator will not have an unexpected grip feeling of the flexible tube structure 41 due to variability in the bending stiffness of the flexible device 22 about the circumferential direction in the course of the entry. Also, it is preferable to set the difference between maximum and minimum levels of the bending stiffness of the variable stiffness device 35 equal to or more than 0.1 time of the bending stiffness of the flexible device 22 including internal structures other than the variable stiffness device 35.

Second Preferred Embodiment

In a structure of the jacket material 49 of a multi-layer form containing resins different in bending stiffness, the bending stiffness of the flexible tube structure 41 varies in the axial direction AD because of thicknesses of plural resin layers. In a structure of the jacket material 49 molded from mixture containing resins different in bending stiffness, the bending stiffness of the flexible tube structure 41 varies in the axial direction AD according to a ratio between amounts of the plural resins. Assuming that the bending stiffness of the flexible tube structure 41 is different in the axial direction AD, the bending stiffness in a given radial direction RD around the axial direction AD is changed at an equal point of the flexible device 22 in the axial direction AD upon occurrence of undulating motion of the coil spring 33 due to its compression with the stiffness controller 34. In the embodiment, a difference between the maximum and minimum bending stiffness of the variable stiffness device 35 is set at most 0.2 time as much as the minimum bending stiffness of the flexible device 22 in the axial direction AD inclusive of internal structures other than the variable stiffness device 35. The reason for the use of the minimum bending stiffness as reference is that recovering property is important for the flexible device 22. Note that it is also possible to set a difference between the maximum and minimum bending stiffness of the variable stiffness device 35 at least 0.1 time as much as the minimum bending stiffness of the flexible device 22 in the axial direction AD inclusive of internal structures other than the variable stiffness device 35.

Third Preferred Embodiment

The variability in the stiffness of the flexible device 22 in the circumferential direction in the course of undulating motion of the coil spring 33 is utilized. For example, the elongated tube 10 is initially advanced into a large intestine of a body of a patient. In general, an operator of the endoscope 12 is likely to manipulate the steering device 21 to direct an upper side of an image of image light to a side of compressing operation of the bending or steering of the steering device 21. Thus, a distal portion of the flexible device 22 is constructed with a feature of easily deformable property by following the steering of the steering device 21. To this end, for example, a bending tendency (easily bendable portion) is imparted to the variable stiffness device 35 initially in such a form that the stiffness of the flexible device 22 in the course of undulating motion of the coil spring 33 (average of plural levels of stiffness at points distributed in the circumferential direction at a predetermined point in the axial direction AD) is lower than the stiffness of the flexible device 22 in the course of bending the steering device 21 to direct the distal end surface 20a upwards (stiffness of the flexible device 22 in the predetermined point in the axial direction AD at a time without undulating motion).

In manufacturing the endoscope 12, a bending device is used for imparting bending tendency (easily bendable portion) to the variable stiffness device 35. Before being combined with the endoscope 12, the coil spring 33 receiving the control wire 31 is supplied to the bending device in a condition of receiving compression force at a constant level.

Figure 17:
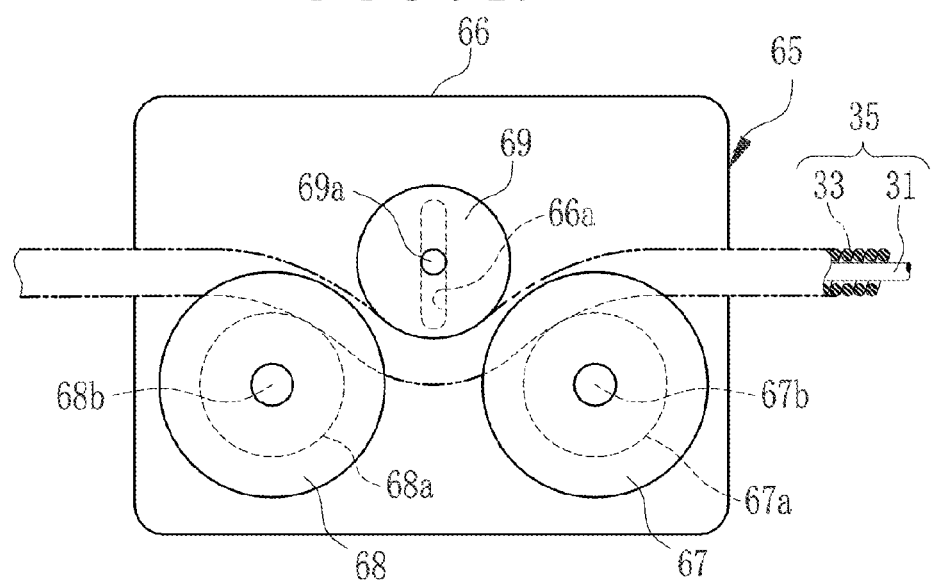
FIG. 17 is a side elevation illustrating a bending mechanism for imparting a bending tendency.

In FIG. 17, a bending device 65 or bending mechanism for imparting a bending tendency (easily bendable portion) to the variable stiffness device 35 is illustrated. The bending device 65 includes a pair of pulleys 67 and 68 and a pressing roller 69 or pulley. A pulley support 66 supports the pulleys 67 and 68 at a predetermined interval. The pressing roller 69 presses the coil spring 33. Pulley grooves 67a and 68a are formed in the pulleys 67 and 68 for receiving the coil spring 33 with the control wire 31 extended through the coil spring 33. A slot 66a is formed in the pulley support 66. The pulleys 67 and 68 have pulley shafts 67b and 68b. The slot 66a is disposed on a line perpendicular to a line that is defined to pass the pulley shafts 67b and 68b. A roller shaft 69a of the pressing roller 69 is movable in the slot 66a. The bending device 65 pushes the coil spring 33 from a side opposite to the side of supporting with the pulleys 67 and 68 upon movement of the pressing roller 69 along the slot 66a, to impart a bending tendency (easily bendable portion) to the variable stiffness device 35 for making this easily bendable in one direction. The variable stiffness device 35 is in an initially deformed condition of plastic deformation of the coil spring 33 and the control wire 31 according to the use with time. It is thus possible to prevent the flexible device 22 from changing in the stiffness in the circumferential direction with time.

Figure 18:
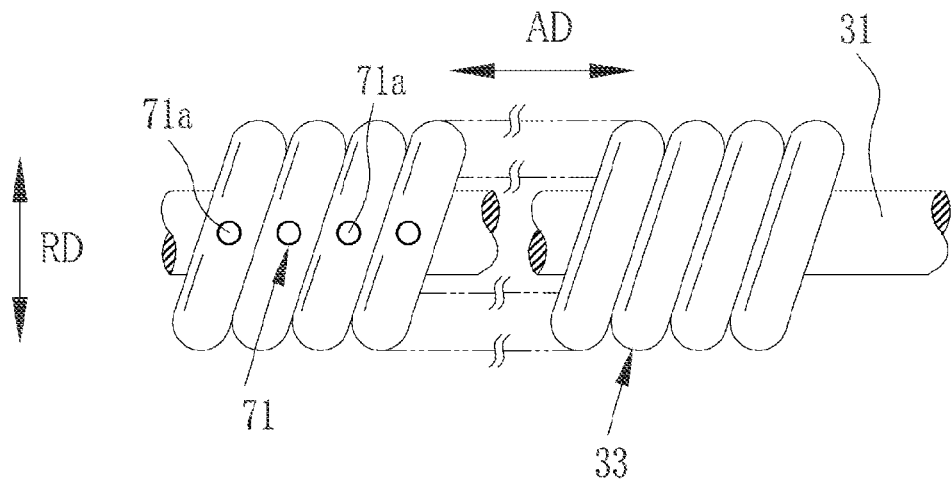
FIG. 18 is a plan illustrating another preferred variable stiffness device having an indicia pattern.

The bending tendency of the variable stiffness device 35 is preferably imparted to direct the distal end surface 20a in one direction, for example, in an upward or downward direction in relation to the image. However, a problem may arise in the course of assembling parts of the endoscope 12 in that a direction in which the bending tendency should be imparted cannot be recognized visually. In FIG. 18, an indicia pattern 71 is initially disposed on the variable stiffness device 35 for indicating a direction of the bending tendency in the course of engagement with the pulleys 67 and 68 of FIG. 17. The indicia pattern 71 is disposed on the periphery of the coil spring 33 because the rotational position of the coil spring 33 and the control wire 31 is kept constant by the retention of the end of the coil spring 33 to the control wire 31. The indicia pattern 71 includes small circles or pattern dots 71a arranged in the axial direction AD in a range of the bending tendency. Also, other elements of a small form can constitute the indicia pattern 71, for example, a line indicia extending in the axial direction AD.

Bendability in response to steering of the steering device 21 is important for the tip device in the elongated tube 10. A preferable range of imparting the bending tendency (easily bendable portion) to the elongated tube 10 is a predetermined length from a distal end of the variable stiffness device 35, for example, 50 cm. Note that the elongated tube 10 is 160 cm long. Furthermore, a bending tendency (easily bendable portion) can be imparted to a proximal portion of the variable stiffness device 35 in the elongated tube 10. This is effective in preventing unexpected shift at the time of twist or the like, because the proximal portion of the flexible device 22 can be prevented from having variation in the stiffness in the circumferential direction. The bending tendency (easily bendable portion) can be imparted to either one of the coil spring 33 and the control wire 31, or to both of those.

Fourth Preferred Embodiment

Figure 19:
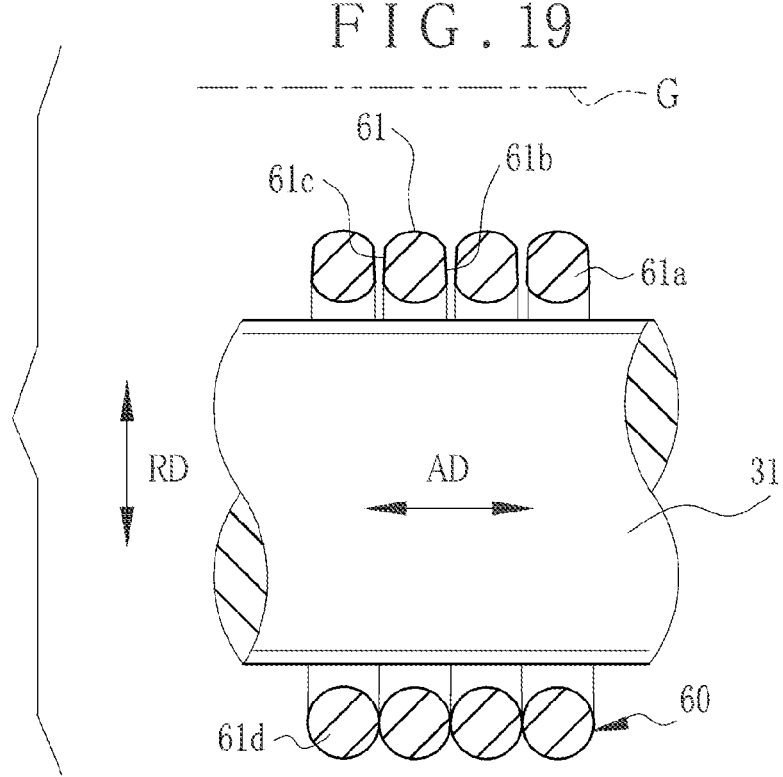
FIG. 19 is a vertical section illustrating another preferred coil spring with chamfered surfaces.
Figure 22:
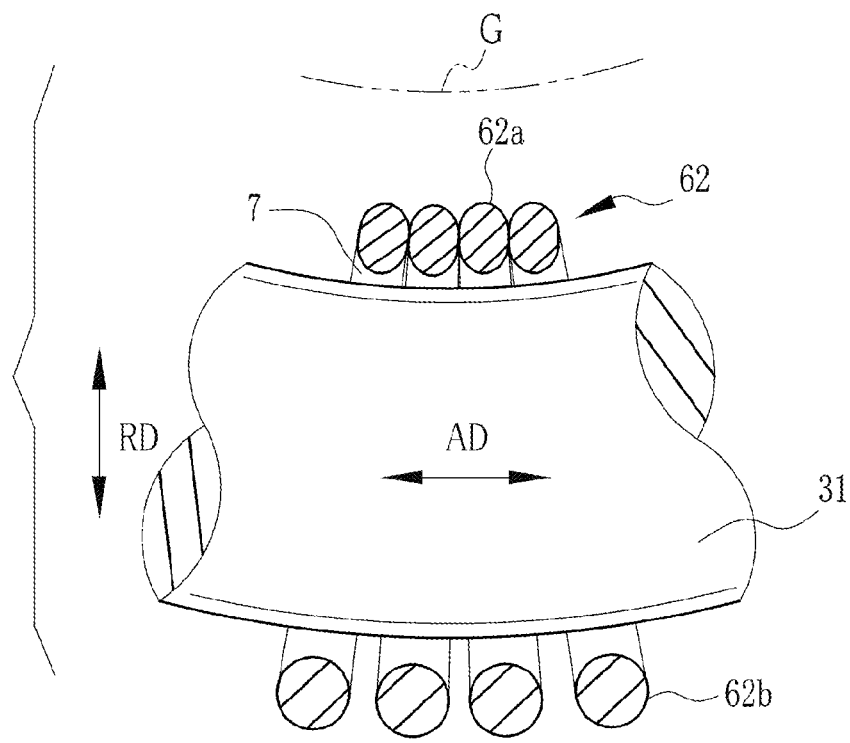
FIG. 22 is a cross section illustrating one preferred coil spring with a feature of a strand cross section.
Figure 23:
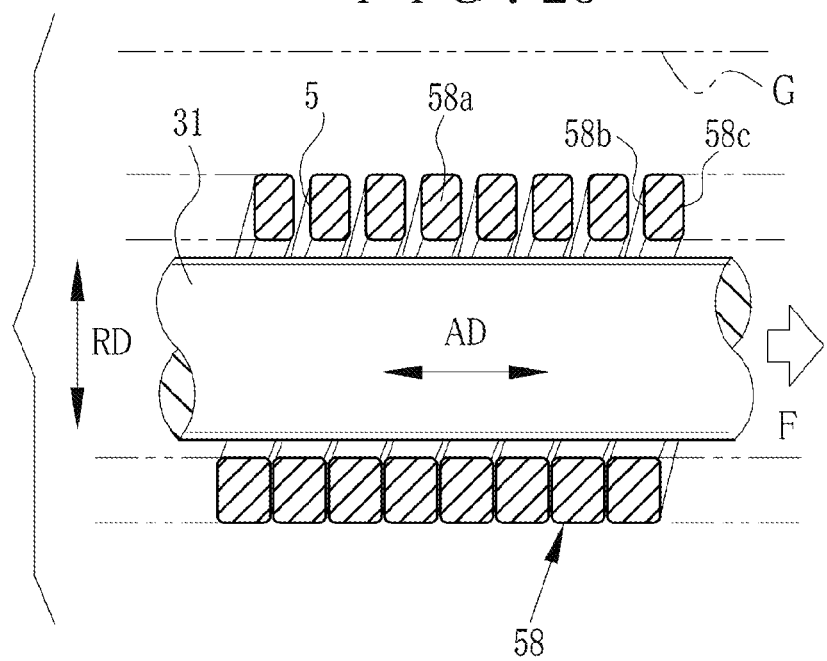
FIG. 23 is a cross section illustrating still another preferred coil spring with a strand cross section of a quadrilateral.

In the third embodiment, the bending tendency is imparted to the variable stiffness device 35 by the bending device. In place of this or in addition to this, a local form of a strand can be modified for the purpose of imparting bending tendency. In FIG. 19, a preferred strand 61 or filament has chamfered surfaces 61b and 61c on a compression side (particular radial direction). In FIG. 22, a preferred coil spring 62 (helical coil) has a portion of which a strand cross section is elliptic. In FIG. 23, a preferred coil spring 58 (helical coil) includes a first portion and a second portion of which a strand cross section has a smaller thickness than that of the first portion.

In FIG. 19, one preferred coil spring 60 (helical coil) including the strand 61 with the chamfered surfaces 61b and 61c for decreasing the strand thickness is illustrated. The chamfered surfaces 61b and 61c are disposed on sides of the strand 61 positioned in a compression side G (particular radial direction) of the compression upon a bending operation so as to facilitate the bend of the distal end surface 20a of the elongated tube 10 in one predetermined direction. The coil spring 60 is wound in a coil form after previously forming the chamfered surfaces 61b and 61c in the strand 61 of a shape with a circular strand cross section.

Figure 20:
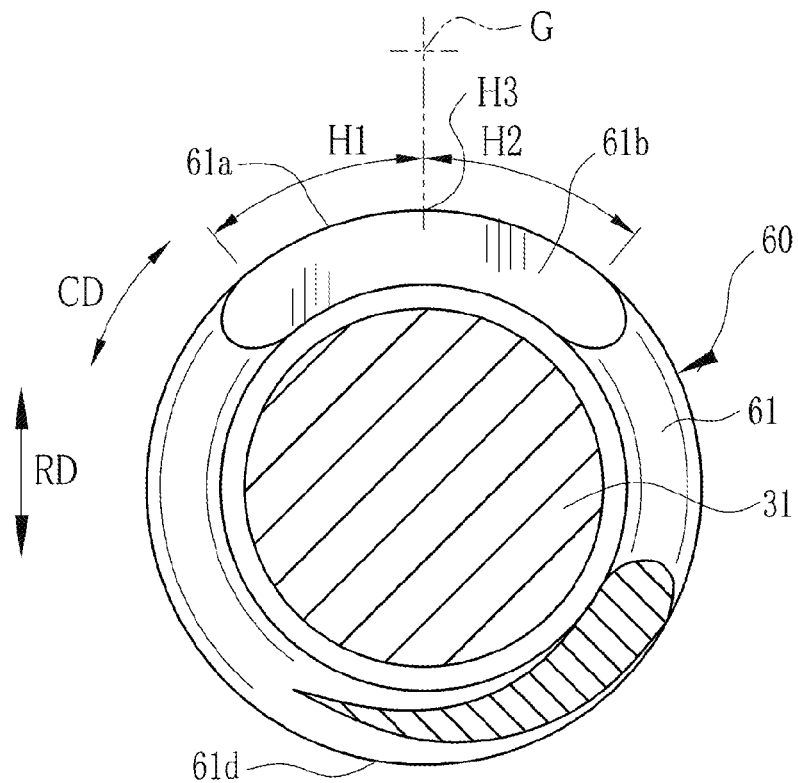
FIG. 20 is a cross section illustrating the coil spring of FIG. 19.

In FIG. 20, an angular range of the chamfered surface 61b is illustrated in a section. The angular range is defined with angles H1 and H2 in the circumferential direction CD in such a manner that the nearest position H3 of a strand portion 61a as an easily bendable portion (having a small thickness) on the compression side G is disposed between the angles H1 and H2. For example, H1 and H2 are equal to or smaller than 90 degrees, and H1+H2 is equal to or smaller than 180 degrees. In operation, the effect of the bending tendency of the strand 61 having the chamfered surface 61b is obtained remarkably in comparison with compression force applied to a well-known strand 61d or filament of a strand cross section of a circular shape. Note that the angular range of the chamfered surface 61c is equal to that of the chamfered surface 61b in FIG. 20.

Figure 21:
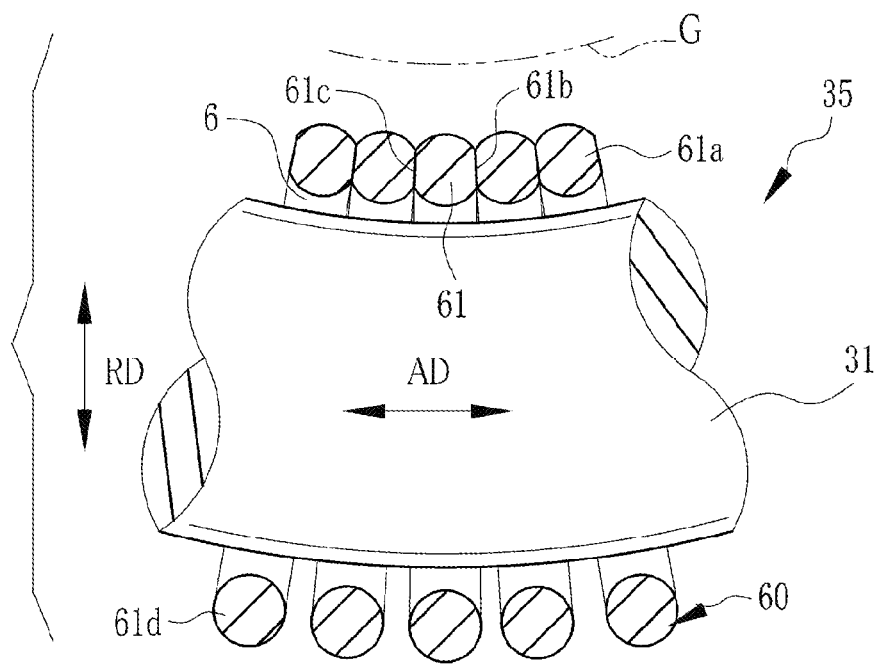
FIG. 21 is a cross section illustrating a curved state of the coil spring.

In FIG. 21, a bent condition of the coil spring 60 is illustrated. In case compression force is applied to the variable stiffness device 35 in the axial direction AD, the variable stiffness device 35 can become easily bent in a direction of locating the strand portion 61a internally with the chamfered surfaces 61b and 61c. In the variable stiffness device 35, a length of tight contact between adjacent coil turns 6 of the strand portion 61a with the chamfered surfaces 61b and 61c is smaller than that between the adjacent coil turns 6 of the strand 61d with a strand cross section of a circular shape. Thus, the radius of curvature of the strand portion 61a on the compression side G can be small. Note that a chamfered surface can be disposed on only one side of the strand 61.

In FIG. 22, the coil spring 62 has a strand 62b or filament, of which a strand portion 62a as an easily bendable portion (having a small thickness) is disposed on a compression side G. The strand portion 62a is characterized in having a locally longer shape (for example, elliptic) in a strand cross section than a remaining portion of the strand 62b (for example, circular) on a pull side in relation to the bend. An area size of tight contact between adjacent coil turns 7 of the strand portion 62a on the compression side G is smaller than an area size of tight contact between the adjacent coil turns 7 of the strand portion 62a on the pull side. Furthermore, it is possible for the strand portion 62a to have a locally longer shape in a strand cross section than a remaining portion of the strand 62b on a pull side in relation to the bend, with a gradual change from the pull side toward the compression side G.

FIG. 23 is a vertical section of the coil spring 58. The coil spring 58 is characterized in a quadrilateral shape of a strand cross section of the strand in a different manner from a well-known circular shape. A strand 58a or filament is wound to constitute the coil spring 58. A pair of chamfered surfaces 58b and 58c for decreasing the strand thickness are disposed on lateral sides of the strand cross section of the strand 58a and located on a compression side G of the compression at the time of receiving the compression force for bending. The shape of the strand 58a as viewed in the strand cross section is quadrilateral and long in the radial direction, so that the use of the coil spring 58 can prevent buckling of a first strand to shift over a strand next to the first strand. In comparison with the coil spring 33 having the strand 33c of a regularly circular shape of a strand cross section in FIG. 6, an area of the contact between adjacent coil turns 5 of the strand can be larger according to FIG. 23 to increase their friction. It is possible to suppress occurrence of undulating motion as occurrence of fine unevenness between the coil turns 5 of the strand 58a can be prevented. Note that various shapes of a strand cross section of the strand 58a other than the quadrilateral shape can be used, for example, a trapezoidal shape, an oval or elliptical shape longer in the radial direction of the coil spring 58.

In the embodiments of FIGS. 19-23, the strand portion 62a of the coil turns 5, 6 and 7 on the compression side (particular radial direction) has a locally longer shape in a strand cross section in relation to bending in the direction of the bending tendency. However, a strand portion of the coil turns on the pull side can have a locally longer shape in the axial direction AD.

In short, an easily bendable portion according to the invention can be constituted by decreasing a thickness of a particular portion of the coil spring 58, 60, 62 or the control wire 31 in a certain direction.

Other variants can be constructed by combining two or more of the features of the above embodiments. For example, the structure of the third embodiment with the bending tendency (easily bendable portion) can be combined with each one of the first and second embodiments.

Figure 24:
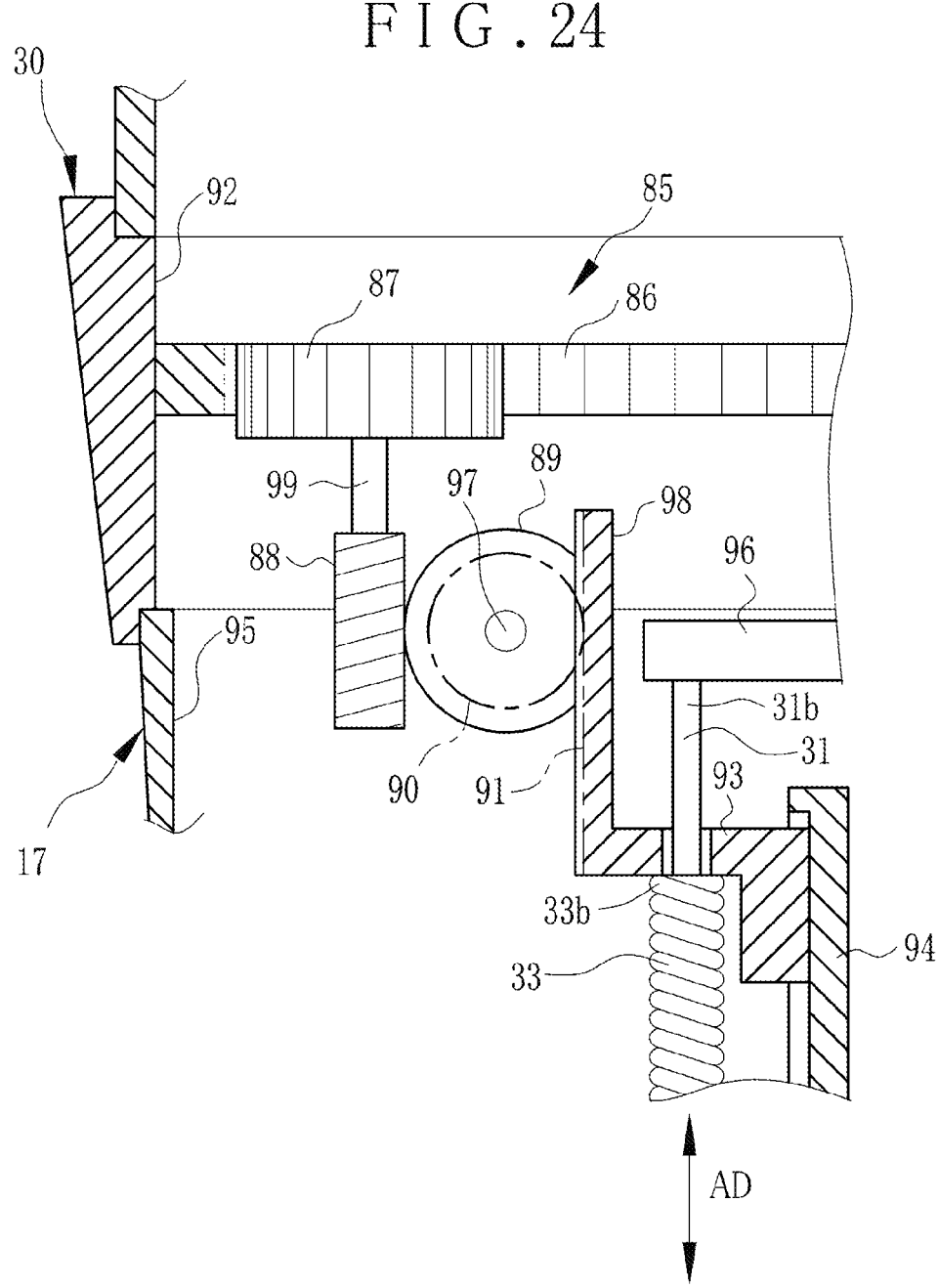
FIG. 24 is a vertical section illustrating another preferred transmission mechanism for moving the coil spring.

Unlike the transmission mechanism 32 of FIG. 7 in which the coil spring 33 is compressed by pulling the control wire 31, another preferred embodiment of FIG. 24 has a feature of moving the coil spring 33 relative to the control wire 31. In FIG. 24, a transmission mechanism 85 includes an inner gear 86, a spur gear 87, a worm gear 88, a worm wheel 89, an intermediate gear 90 and a rack gear 91. The control wheel 30 has an inner wall 92, on which the inner gear 86 is formed, and meshed with the spur gear 87. The spur gear 87 has a gear shaft 99, on which the worm gear 88 is rotatable together. The worm wheel 89 is meshed with the worm gear 88. The worm wheel 89 has a wheel axis 97, on which the intermediate gear 90 is rotatable together. The rack gear 91 is meshed with the intermediate gear 90. There is a slider 98 (rack bar) having the rack gear 91. A slidable end stopper 93 is disposed to extend from the slider 98 and retains the proximal coil end 33b of the coil spring 33. A slide rail 94 supports the end stopper 93 in a slidable manner. The grip handle 17 has a handle housing 95. A support plate 96 is incorporated in the handle housing 95. The proximal wire end 31b of the control wire 31 is retained on the support plate 96.

In case the control wheel 30 is rotated, the spur gear 87 meshed with the inner gear 86 is driven in the transmission mechanism 85. The worm gear 88 and the worm wheel 89 are rotated by the rotation of the spur gear 87. The intermediate gear 90 is rotated with the wheel axis 97 and the worm wheel 89, to move the rack gear 91 linearly in mesh therewith. As a result, the transmission mechanism 85 shifts the end stopper 93 on the slider 98 in the axial direction AD in response to rotation of the control wheel 30, to change the compression force applied to the coil spring 33.

Figure 25:
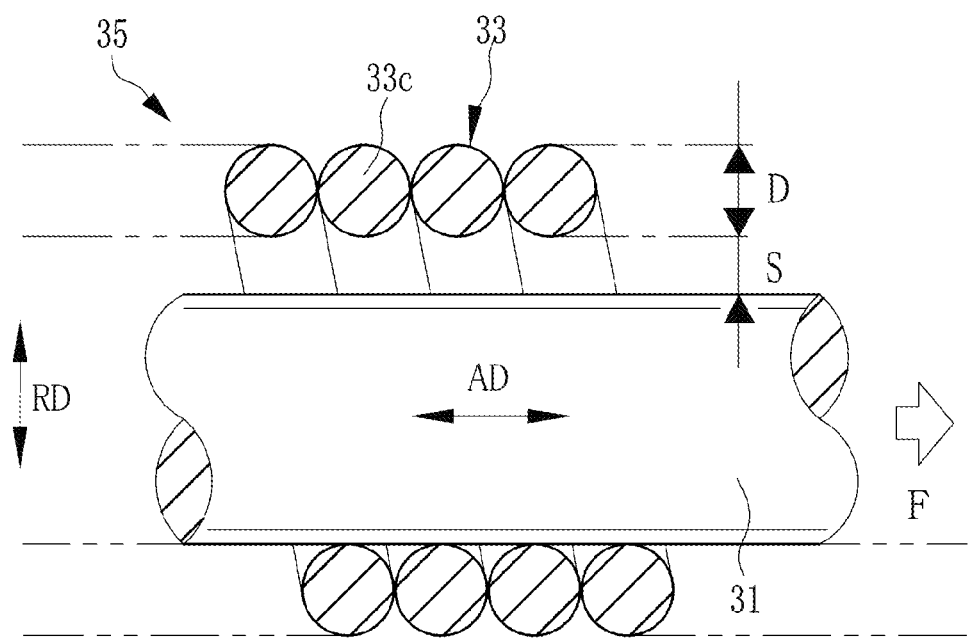
FIG. 25 is a cross section illustrating a relationship between a clearance space around the wire and a strand thickness of a strand.

In conclusion, the following effect is obtained. In FIG. 25, a relationship of a clearance space S between the coil spring 33 and the control wire 31 to a strand thickness D of the strand 33c in the radial direction is illustrated. The clearance space S is set smaller than the strand thickness D (or cross sectional diameter assuming that the strand 33c is circular in the strand cross section). As described with FIG. 14, the stiffness controller 34 adjusts the stiffness in a range of the stiffness slightly short of the bending stiffness E1 upon starting undulating motion of the coil spring 33. Consequently, the stiffness is adjusted in a range free from occurrence of undulating motion of the coil spring 33. No variability of the stiffness in the circumferential direction CD occurs upon the undulating motion. An operator can handle the endoscope without unwanted grip feeling in the course of the bending operation.

Note that the position of the distal coil end 33a of the coil spring 33, 58, 60, 62, namely the length of the coil spring 33 in the axial direction, is not limited to the above embodiments. The distal coil end 33a of the coil spring 33 can be disposed close to a distal end portion of the flexible device 22. However, it is highly preferable for the coil spring 33 to have such a suitable length as to achieve effects by way of the variable stiffness device 35.

In short, the endoscope includes the elongated tube having the flexible tube structure. The wire is fixedly retained on the end of the coil spring and disposed through the coil spring. The variable stiffness device includes the coil spring and the wire, and disposed inside the flexible tube structure. The stiffness controller compresses the coil spring to adjust stiffness of the flexible tube structure. The clearance space between the coil spring and the wire is smaller than a size of the strand of the coil spring in the radial direction. The stiffness controller adjusts the stiffness in the stiffness range of the flexible tube structure slightly smaller than the stiffness at the time of starting undulating motion of the spring.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope having an elongated tube for entry in a body cavity and imaging of an object, comprising:
   a flexible tube structure for constituting said elongated tube;
   a coil spring, contained in said flexible tube structure to extend in an axial direction, for constituting a variable stiffness device;
   a wire disposed to extend in said axial direction, received through said coil spring, a distal end of said coil spring being retained on said wire, for constituting said variable stiffness device;
   an internal structure contained in said flexible tube structure;
   an externally operable stiffness controller for changing coil tightness of said coil spring by use of said wire, to adjust bending stiffness of said elongated tube;
   wherein in case said bending stiffness is changed in one radial direction at an equal point with reference to said axial direction, a difference between maximum and minimum levels of bending stiffness of said variable stiffness device is at most 0.2 time as much as bending stiffness of said flexible tube structure inclusive of said internal structure other than said variable stiffness device upon occurrence of undulating motion of said coil spring in response to compression force of said stiffness controller to said coil spring.

2. An endoscope as defined in claim 1, wherein said stiffness controller includes:
   a take-up pulley on which a proximal end of said wire is retained, said take-up pulley winding said wire in said axial direction;
   a control wheel rotatable around said axial direction;
   a first bevel gear caused to rotate by said control wheel;
   a second bevel gear, meshed with said first bevel gear, for transmitting rotation to said take-up pulley.

3. An endoscope as defined in claim 1, wherein said stiffness controller includes:
   a slider, movable in said axial direction, for sliding a proximal end of said coil spring relative to a proximal end of said wire;
   a control wheel rotatable around said axial direction;
   an intermediate gear caused to rotate by said control wheel;
   a rack gear, meshed with said intermediate gear, for moving in said axial direction, to transmit movement to said slider.

4. An endoscope having an elongated tube for entry in a body cavity and imaging of an object, comprising:
   a flexible tube structure for constituting said elongated tube, wherein bending stiffness of said flexible tube structure is different in an axial direction;
   a coil spring, contained in said flexible tube structure to extend in said axial direction, for constituting a variable stiffness device;
   a wire disposed to extend in said axial direction, received through said coil spring, a distal end of said coil spring being retained on said wire, for constituting said variable stiffness device;
   an internal structure contained in said flexible tube structure;
   an externally operable stiffness controller for changing coil tightness of said coil spring by use of said wire, to adjust said bending stiffness of said elongated tube;
   wherein in case said bending stiffness is changed in one radial direction at an equal point with reference to said axial direction, a difference between maximum and minimum levels of bending stiffness of said variable stiffness device is at most 0.2 time as much as minimum bending stiffness of said flexible tube structure inclusive of said internal structure other than said variable stiffness device in said axial direction upon occurrence of undulating motion of said coil spring in response to compression force of said stiffness controller to said coil spring.

* * * * *